US008575427B2

(12) United States Patent
Wang et al.

(10) Patent No.: US 8,575,427 B2
(45) Date of Patent: Nov. 5, 2013

(54) ***CHORISMATE MUTASE* GENE FROM THE POTATO CYST NEMATODE *GLOBODERA ROSTOCHIENSIS***

(75) Inventors: Xiaohong Wang, Ithaca, NY (US); Shunwen Lu, Fargo, ND (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 936 days.

(21) Appl. No.: 12/460,813

(22) Filed: Jul. 24, 2009

(65) Prior Publication Data

US 2012/0046339 A1 Feb. 23, 2012

Related U.S. Application Data

(60) Provisional application No. 61/188,694, filed on Aug. 12, 2008.

(51) Int. Cl.

| | |
|---|---|
| ***C12N 15/87*** | (2006.01) |
| ***C12N 15/64*** | (2006.01) |
| ***C12N 15/74*** | (2006.01) |
| ***A01H 1/02*** | (2006.01) |
| ***C12P 21/06*** | (2006.01) |
| ***C12P 19/34*** | (2006.01) |

(52) U.S. Cl.

USPC ........... 800/285; 800/288; 800/294; 800/265; 435/69.1; 435/91.21; 435/91.4; 435/91.51; 435/468

(58) Field of Classification Search

None

See application file for complete search history.

(56) References Cited

U.S. PATENT DOCUMENTS

2005/0188438 A1 * 8/2005 Ren et al. ...................... 800/279

OTHER PUBLICATIONS

Popeijus et al, Nematology, 2, pp. 567-574, 2000.*

* cited by examiner

*Primary Examiner* — Anne Grunberg
*Assistant Examiner* — Stephen Uyeno
(74) *Attorney, Agent, or Firm* — John D. Fado; Evelyn M. Rabin

(57) ABSTRACT

The nucleotide sequence of a 992 bp region of cDNA and the nucleotide sequence of a 1973 bp (or a 1913 bp) of genomic DNA of the Gr-cm-1 gene were determined for *G. rostochiensis*. PCR primers and probes specific for *G. rostochiensis* and *G. pallida* were generated. PCR assays, including a real-time TaqMan PCR were used to identify *G. rostochiensis* and *G. pallida* and to differentiate *G. rostochiensis* from *G. pallida*. Transgenic hairy roots expressing Gr-cm-1 dsRNA were generated. There was a 52% reduction in the average number of females per root in the Gr-cm-1 dsRNA transgenic lines when compared with the infected control lines.

9 Claims, 8 Drawing Sheets
(5 of 8 Drawing Sheet(s) Filed in Color)

```
Gp-cm-1         AATGGACTCAAATTTGTTGTTGGGATGGAAGGCCAAACGGAAACGGAATCCCCAACGGAA 826
Gr-cm-1         GATGGATTCAAATTTGTTGTTGGGATGGAAGGCCAAACGGAAACGGAATCGACAACGGGA 981
                 ***** ****************************************  ****** *
          GpCM1-829F (Gp-specific primer, highlighted in green)     Intron-2/start
Gp-cm-1         AAC[illegible]TAATAATTTTATGTGTTGTAAGCCAAATCAAGgtacggtc 886
Gr-cm-1         AA------------------TAATATTTTTATGTGTTGTAAGCCGAATCAAGgtacggtc 1023
                **                  ***** ****************** **************
                  GpCM1-925R (Gp-specific primer, highlighted in green)
Gp-cm-1         actaaacggaaaga[illegible]ttttcgatatggtcatttttttg 946
Gr-cm-1         actaaatggaaaga------------------aaaatcttttcgatttgaccatttttttg 1065
                ****** *******                  * ************ **  *********
                            Intron-2/end
Gp-cm-1         ggccgtctgtaaccatttcaccagAGACGGCCACACTCTTCATTGTCGGCGTGGCCAGC 1006
Gr-cm-1         c-ccgtctgtaaccattttgaccagAGACGGCCACTCTCTTCATTGTCGGCATGGCCAAC 1124
                  **************** *************** *************** ****** *

Gp-cm-1         AAACGGCTGATGTTGGCCAAAGACGTGGCTCTCTACAAGTACATCAACAACAATAGCATT 1066
Gr-cm-1         AAACGGCTGATGTTGGCCAAAGATGTGGTTCTCTACAAGTACATCAACAACAATAGCATT 1184
                *********************** **** *******************************

Gp-cm-1         GACGATTTTGAGCGTGAAAAGGTTGTGTTGCAAAATGTTTTGGCTCAAGCGAAAAGTGCC 1126
Gr-cm-1         GACGATTTCGAGCGGGAAAAGGTTGTGCTGCAAAATGTTTTGGCTCAGGCGAAGAGTGCC 1244
                ******** ***** ************ ******************* ***** ******
                                                        GpCM-1079F/GrCM-1290F
Gp-cm-1         GGCATAAGCGACAACTACGGGGAGCCGTTCTTCCAAGACCAAATG[illegible] 1186
Gr-cm-1         GGGATAAGCGACAACTACGGGGAGCCGTTTTTCCAAGACCAAATG[illegible] 1304
                ** ************************** ******************************
                     Intron-3/start
Gp-cm-1         [illegible]gtaaaaaaggtttaggcttaattaacatatttaaaa-ttgtggaccagatctgt 1245
Gr-cm-1         [illegible]gtaaaaaaggtttaggtttaattaacatatttaaaaattgtggagaagatctgt 1364
                ********************** ******************* *******  ********
                  GpCM-1263F (Gp-cm-1 specific TaqMan probe, highlighted in red)
Gp-cm-1         tcggtaccagcgacatt[illegible]aatgacaatttattgcc 1305
Gr-cm-1         TTAGTGCCAACGACATTTGAAGCGC-------------AATTAAATCACAATTTATTGCC 1411
                *  ** *** ***************              ******** *************

Gp-cm-1         caggggcttaatattctcaaattgcttcttctcatttgaagcgctgttctttcaataaat 1365
Gr-cm-1         cagcg------------------------------------------------------- 1416
                *** *
                                                              GpCM1-1551F (blue
                                     color highlighted nucleotide sequence)
Gp-cm-1         taaataacaatttattgcccaggggcttaatattctcaaattgcttcttctcatttgaag 1425
Gr-cm-1         -------------------------cttaataatctctaattgcttcttcccatttgaag 1451
                                         ******* **** ************ *********
                  GpCM-1357R/GrCM-1475R
Gp-cm-1         c[illegible]gtttgattggttgagaaaaagctacagcgcttcaa 1485
Gr-cm-1         t[illegible]gtttgggtggttgacaaaaagctaaagcgcttcaa 1511
                 ***************************  ******* ********* **********

                                                    Intron-3/end
Gp-cm-1         att[illegible]---[illegible]--[illegible]ggaaactttttgtagAAGGGCTACGTGA 1540
Gr-cm-1         atttcctatcgaattgaatagtgaggcgtaccgtgaaacctttttgtagAAGGGCTACGTGA 1571
                *** *  *    *  ***    ****** ***** ***** ********************

Gp-cm-1         AGACGTGGAACATCAAAGGGTCGTCGCCGTCTCAGACAGTGCCCG[illegible] 1600
Gr-cm-1         AGATGTGGAACATCGGAGGGCCGTCGCCGTCTCAGACGGTGCCCGACCTGCAGACGATCA 1631
                *** **********    **** **************** ********* ******** ***

Gp-cm-1         [illegible]CGTCCCAAAGTGACGGAGGCAACAGCCGACATGGTGTTGGCACTGAAAACGTTCCAAT 1660
Gr-cm-1         CCCGTCCCAAGGTGACGGAGGCAACTGCCGACATGGTATTGGCACTGAAAACCTTCCAAA 1691
                ********** ************** *********** ************** ******

Gp-cm-1         TGTTTCGTAACAAATCGAATTGTTGGAGTTTGCTGGAACATAAACAGACAATGACCGGCA 1720
Gr-cm-1         CGTTTCGCAACAAATCGAATTGTTGGCGTTTGCTGGAACATAAACAGACAATGACCGGCA 1751
                 ****** ****************** ********************************

Gp-cm-1         ATTTTCTGAGTTTGAACGAGCCGAACGGTGTGGAAGCCTTCCGAAAAGCGGTGGTCCGAC 1780
Gr-cm-1         ATTTTCTGAGTTTGAACCAGCCGAACGGTCTGGACGCCTTCCGAAAAGCGGTGGTCCGAC 1811
                ********************************** *************************

Gp-cm-1         TGTGTGGCCAGGAACCGGAACAAAACACAGTGCACGCCATTGACGAAAAGGCCAAGAAAC 1840
```

Fig. 1B

```
Gr-cm-1    TGTGCGGCCAGGAGCCGAAACAAAACACAGTGCACGACATTGACGAGCAGGCCAAGAAAC 1871
           **** ******** *** ***************** *********  ***********

Gp-cm-1    TGCTGAATGAATGA---------------------------------------------- 1854
Gr-cm-1    TGCTGAATGAATGA---------------------------------------------- 1885
           **************
```

Fig.1C

```
Gp-cm-1    ggtttaattacccaagtttgagaaaaATGAATTTGTTAGTCGTTCCGTTTTTTCTGTCGC 60
Gr-cm-1    ggtttaattacccaagtttgagaacaATGAATTTGTTGGTCGTTCCGTTTTTTCTGTCGC 60
           ************************* ************ **********************

Gp-cm-1    TTTTTTTGCCATTTGCACCCGCACCAAAATCGCCCGCTCGTCGTGCTGATGCGAATCGAC 120
Gr-cm-1    TTTTTTTGCCATTTGCTCCCGCAGCAAAATCGCCCGCTCGTCGTGCTGTTGCAAATCGTC 120
           **************** ****** *********************** *** ***** *

Gp-cm-1    AAAATGATCGTATAAACTGCGAGAAGCATTGCACTAATTATTACCTAGCCGAAAACAACA 180
Gr-cm-1    AAAATGGTCATATAAACTGCGAAAAGCATTGCACTGATCATTACCTAACCGAAAACAACA 180
           ****** ** ************ ************ ** ******** ************

Gp-cm-1    AATGCAAGTCATCGGAGGAAATCATTTTGCGCAAGTCCGACTGTGCCTTCATGAAGAACA 240
Gr-cm-1    AATGCAAGTCATCGGAGGAAGTCATTTTGCGCAAGTCCGACTGTGCCTTCATGAAGAGCA 240
           ******************** ************************************ **

Gp-cm-1    TTGAGAATGGACTCAAATTTGTTGTTGGGATGGAAGGCCAAACGGAAACGGAATCCCCAA 300
Gr-cm-1    TTGAGTATGGATTCAAATTTGTTGTTGGGATGGAAGGCCAAACGGAAACGGAATCGACAA 300
           ***** ***** *******************************************  ***

Gp-cm-1    CGGAAAACGCCCCAACAGCCAACAATAATAATTTTATGTGTTGTAAGCCAAATCAAGAGA 360
Gr-cm-1    CGGGAAA------------------TAATATTTTTATGTGTTGTAAGCCGAATCAAGAGA 342
           *** ***                  ***** ***************** **********

Gp-cm-1    CGGCCACACTCTTCATTGTCGGCGTGGCCAGCAAACGGCTGATGTTGGCCAAAGACGTGG 420
Gr-cm-1    CGGCCACTCTCTTCATTGTCGGCATGGCCAACAAACGGCTGATGTTGGCCAAAGATGTGG 402
           ******* *************** ****** ************************ ****

Gp-cm-1    CTCTCTACAAGTACATCAACAACAATAGCATTGACGATTTTGAGCGTGAAAAGGTTGTGT 480
Gr-cm-1    TTCTCTACAAGTACATCAACAACAATAGCATTGACGATTTCGAGCGGGAAAAGGTTGTGC 462
            *************************************** ***** ************

Gp-cm-1    TGCAAAATGTTTTGGCTCAAGCGAAAAGTGCCGGCATAAGCGACAACTACGGGGAGCCGT 540
Gr-cm-1    TGCAAAATGTTTTGGCTCAGGCGAAGAGTGCCGGCATAAGCGACAACTACGGGGAGCCGT 522
           ******************* ***** ******** ************************

Gp-cm-1    TCTTCCAAGACCAAATGGACGCTAACAAAGTCATTCAGAACGGCTACGTGAAGACGTGGA 600
Gr-cm-1    TTTTCCAAGACCAAATGGACGCTAACAAAGTCATTCAGAACGGCTACGTGAAGATGTGGA 582
           * ***************************************************** *****

Gp-cm-1    ACATCAAAGGGTCGTCGCCGTCTCAGACAGTGCCCGACTTGCAGACGGTCACCCGTCCCA 660
Gr-cm-1    ACATCGGAGGGCCGTCGCCGTCTCAGACGGTGCCCGACTTCCAGACGATCACCCGTCCCA 642
           *****  **** **************** *********** ******* ***********

Gp-cm-1    AAGTGACGGAGGCAACAGCCGACATGGTGTTGGCACTGAAAACGTTCCAATTGTTTCGTA 720
Gr-cm-1    AGGTGACGGAGGCAACTGCCGACATGGTATTGGCACTGAAAACCTTCCAAACGTTTCGCA 702
           * ************** *********** ************** ******  ****** *

Gp-cm-1    ACAAATCGAATTGTTGGAGTTTGCTGGAACATAAACAGACAATGACCGGCAATTTTCTGA 780
Gr-cm-1    ACAAATCGAATTGTTGGCGTTTGCTGGAACATAAACAGACAATGACCGGCAATTTTCTGA 762
           ***************** ******************************************

Gp-cm-1    GTTTGAACGAGCCGAACGGTGTGGAAGCCTTCCGAAAAGCGGTGGTCCGACTGTGTGGCC 840
Gr-cm-1    GTTTGAACGAGCCGAACGGTGTGGACGCCTTCCGAAAAGCGGTGGTCCGACTGTGCGGCC 822
           ************************* ***************************** ****
```

Fig. 4A

```
Gp-cm-1    AGGAACCGGAACAAAACACAGTGCACGCCATTGACGAAAAGGCCAAGAAACTGCTGAATG 900
Gr-cm-1    AGGAGCCGAAACAAAACACAGTGCACGACATTGACGAGCAGGCCAAGAAACTGCTGAATG 882
           **** *** ****************** *********  *********************

Gp-cm-1    AATGAcccgacggaat-tgtgccaaccaatttggtgtgatttatttggatcctaaacccc 959
Gr-cm-1    AATGAcc-gacggaatatgtgtcaaccaatttagtgtgatttatttagatcctacgccc- 940
           ******* ******** **** ********** ************* *******  ***

Gp-cm-1    tatgtttggagattagctgttagtaaaaacttaccattcgacaaaaaaaaaa- 1011
Gr-cm-1    tatgtgtggagattagatga-agtaaaaacctgacaaaaaaaaaaaaaaaaaa 992
           ***** ********** **  ********* *  **     * **********
```

Fig. 4B

*CHORISMATE MUTASE* GENE FROM THE POTATO CYST NEMATODE *GLOBODERA ROSTOCHIENSIS*

This application claims the benefit of U.S. Provisional Application No. 61/188,694, filed Aug. 12, 2008, which is incorporated herein by reference in its entirety.

BACKGROUND OF THE INVENTION

1. Field of the Invention

This invention relates to a novel *chorismate mutase* (cm) gene, cloned from the potato cyst nematode *Globodera rostochiensis*, sequence polymorphisms in the *Globodera* cm genes, species-specific PCR (polymerase chain reaction) assays for specifically identifying *G. rostochiensis* and differentiating *G. rostochiensis* from *G. pallida*, and a strategy for developing *G. rostochiensis*-resistant potato cultivars.

2. Description of the Relevant Art

Potato cyst nematodes, *G. rostochiensis* and *G. pallida*, are internationally-recognized quarantine pests and considered the most devastating pests of potatoes due to annual worldwide yield losses estimated at 12.2%. First seen in the United States in 1941 on Long Island, *G. rostochiensis* was kept in check first with pesticides and later by crop rotation and planting of nematode-resistant potato varieties. These strategies had helped confine the pest to nine New York counties. Potato cyst nematodes continue to spread throughout North America and were recently detected in Idaho (*G. pallida*) and Quebec and Alberta, Canada (*G. rostochiensis*) creating serious problems for the potato industry, increasing the risk for the spread of these nematodes into other potato producing states, and resulting in a reevaluation of current quarantine practices.

*G. rostochiensis* is a sedentary endoparasitic nematode that has evolved an intimate parasitic relationship within host plant roots by transforming selected root cells into elaborate feeding structures that provide the nutrients required for the development and reproduction of the nematode. This root-infesting pest is nearly impossible to rid from contaminated soil because its eggs can lie dormant, protected within the dead body of its parent, for up to 30 years.

The endemic pathotype of *G. rostochiensis*, Ro1, continues to spread within New York state and a new pathotype, Ro2, that is virulent on potato cultivars resistant to Ro1, has become established in the field. Previously, more than 30 potato varieties that resist the original nematode race, Ro1, had been introduced. The key to Ro1 resistance is a potato gene called H1; however, H1 has no effect on the new nematode pathotype Ro2. To date, there are no commercially-available potato cultivars resistant to Ro2. If Ro2 were to become established in potato, tomato, and eggplant fields, it would cause significant annual losses.

Determining the *G. rostochiensis* pathotype with a traditional bioassay takes almost two years, during which time potato growers cannot determine if their fields contain Ro2. If Ro2 is found, the farmer is forced to abandon potato production or grow a non-profitable European variety, Sante. Thus, for eradication and quarantine purposes, there is a need for an assay to identify the *G. rostochiensis* pathotypes more quickly.

PCR-based assays have been described for detection and speciation of *Globodera*. The Random Amplified Polymorphic DNA (RAPD) method was used to determine inter- and intra-specific variation between populations of *Globodera rostochiensis* and *G. pallida* (Folkertsma et al. 1994. *Phytopathology* 84: 807-811). Two other published PCR methods for discrimination of potato cyst nematode species used a multiplex PCR with three primers based on the potato cyst nematode ribosomal internal transcribed spacer (ITS) region sequences: species-specific primers for *G. rostochiensis* and *G. pallida* in combination with a common primer which amplifies both (Mulholland et al. 1996. *BCPC Symp. Proc.* 65: 247-252; Bulman and Marshall. 1997. *NZ J. Crop Hortic. Sci.* 25: 123-129). The development of genotypic methods with the ability to precisely discriminate among the different species of *Globodera* is essential for effective monitoring and surveillance to determine the prevalence of these organisms in the environment, to facilitate implementing specific disease control strategies, and for accurately selecting areas for quarantine. There still exists a need for specific primers and methods capable of specifically identifying and differentiating pathogenic *Globodera* species. Nematode parasitism genes play important roles in nematode infection and parasitism of host plants and they have been suggested to have evolved much more quickly than ribosomal DNA; therefore, the parasitism gene, cm, isolated from the nematode is expected to be more suitable for the development of diagnostic methods/markers that distinguish *Globodera* species within a genus.

Plant-mediated RNA interference (RNAi) has been used to target nematode parasitism genes and helped attain broad resistance against four root-knot nematode species in the model plant *Arabidopsis* (Huang et al. 2006. *Proc. Natl. Acad. Sci. USA* 103: 14302-14306). The double-stranded (dsRNA) or small interfering (siRNA) molecules were taken up by the nematode from soaking solution (in vitro) or from plant tissue (in planta). RNAi has been observed to function in both cyst and root-knot nematode species (Lilley et al. 2007. *Molecular Plant Path.* 8: 701-711). Production of parasite-specific dsRNA in plant cells has been suggested as a novel and durable strategy for control of plant parasitic nematodes including cyst nematodes (e.g. Gheysen and Vanholme. 2007. *Trends in Biotech.* 25: 89-92; Steeves et al. 2006. *Func. Plant Biol.* 33: 991-999).

The use of nematode resistant cultivars is the most economical and environmentally-safe means of nematode control; therefore, there is also a need for Ro2-resistant cultivars.

SUMMARY OF THE INVENTION

We have cloned and sequenced cm, a novel chorismate mutase gene from the potato cyst nematode *Globodera rostochiensis*, and have confirmed its expression within the subventral gland cells of *G. rostochiensis*. We have identified sequence polymorphisms between cm genes from *G. rostochiensis* and *G. pallida*.

In accordance with this discovery, it is an object of the invention to provide isolated novel oligonucleotides for use as primers and probes for species-specific PCR (polymerase chain reaction) assays for specifically identifying *G. rostochiensis* and differentiating *G. rostochiensis* from *G. pallida.*

It is a further object of the invention to provide the novel DNA sequence for encoding *G. rostochiensis* cm for a comparison to the DNA sequence for encoding *G. pallida* cm for a strategy for developing PCR primers based upon the nucleotide differences identified in the 1973 bp DNA sequence of *G. rostochiensis* cm gene and the 1854 bp DNA sequence of *G. pallida* cm gene.

It is another object of the invention to provide a TaqMan PCR assay method and a standard PCR assay method utilizing the novel primers and probes to differentiate *G. rostochiensis* from *G. pallida.*

It is an additional object of the invention to monitor the effectiveness of quarantine and eradication protocols utilizing the novel primers and probes.

It is yet another object of the invention to provide a strategy of developing *G. rostochiensis*-resistant potato cultivars.

It is a still further object of the invention to provide nucleic acid compositions homologous to a portion of the chorismate mutase gene of *G. rostochiensis*, said compositions for controlling *G. rostochiensis* infection and parasitism of potatoes, tomatoes, and eggplants.

It is an additional object of the invention to provide a method for controlling the infection of a plant by a parasitic *G. rostochiensis* nematode, comprising the steps of contacting the nematode with a dsRNA molecule comprising one strand that is substantially identical to a portion of chorismate mutase gene, thereby controlling the infection of the plant by the *G. rostochiensis* nematode.

It is another object of the invention to provide a method for modifying or inhibiting the expression of the chorismate mutase gene in *G. rostochiensis* cells, the method comprising: transforming plant hairy roots with a vector comprising a nucleic acid sequence encoding a dsRNA operatively linked to a promoter and a transcription termination sequence, selecting for transformed plant hairy roots that have integrated the nucleic acid sequence into their genomes, screening the transformed plant hairy roots for expression of the dsRNA encoded by the nucleic acid sequence, and selecting plant hairy roots that express the dsRNA and/or siRNA.

It is an additional object of the invention to provide a double stranded ribonucleotide sequence produced by preparing a recombinant polynucleotide sequence comprising a first and a second polynucleotide sequence, wherein the first polynucleotide sequence comprises an isolated polynucleotide sequence homologous to a portion of said chorismate mutase gene of *G. rostochiensis*, wherein the second polynucleotide sequence is substantially the reverse complement of the first polynucleotide sequence such that the first and the second polynucleotide sequences hybridize when transcribed into a ribonucleic acid to form the double stranded ribonucleotide molecule. Inhibition of *G. rostochiensis* growth and development is accomplished by inhibiting expression of a nucleotide sequence in the *G. rostochiensis* that is complementary to the sequence of the first polynucleotide.

It is an additional object of the invention to provide a vector which comprises the construct which comprises the two polynucleotide sequences described above operably linked to a heterologous promoter functional in a plant cell.

It is another object of the invention to provide plant roots transformed by said vector, wherein said plant roots are potato, tomato, or eggplant roots.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 2A depicts an amplification plot showing amplification of a targeted DNA fragment. FIG. 2B depicts an amplification plot depicting no amplification of a targeted DNA fragment. NTC=no template control.

FIG. 4 depicts the cDNA sequence alignment between *G. rostochiensis* (SEQ ID NO: 4) and *G. pallida* (SEQ ID NO: 5) cm genes. The region used for generating dsRNA targeting Gr-cm-1 in transgenic plants was highlighted in yellow. The cm genes from *G. rostochiensis* and *G. pallida* share a 91.6% nucleotide identity in their open reading frames.

DETAILED DESCRIPTION OF THE INVENTION

Figure 1A:
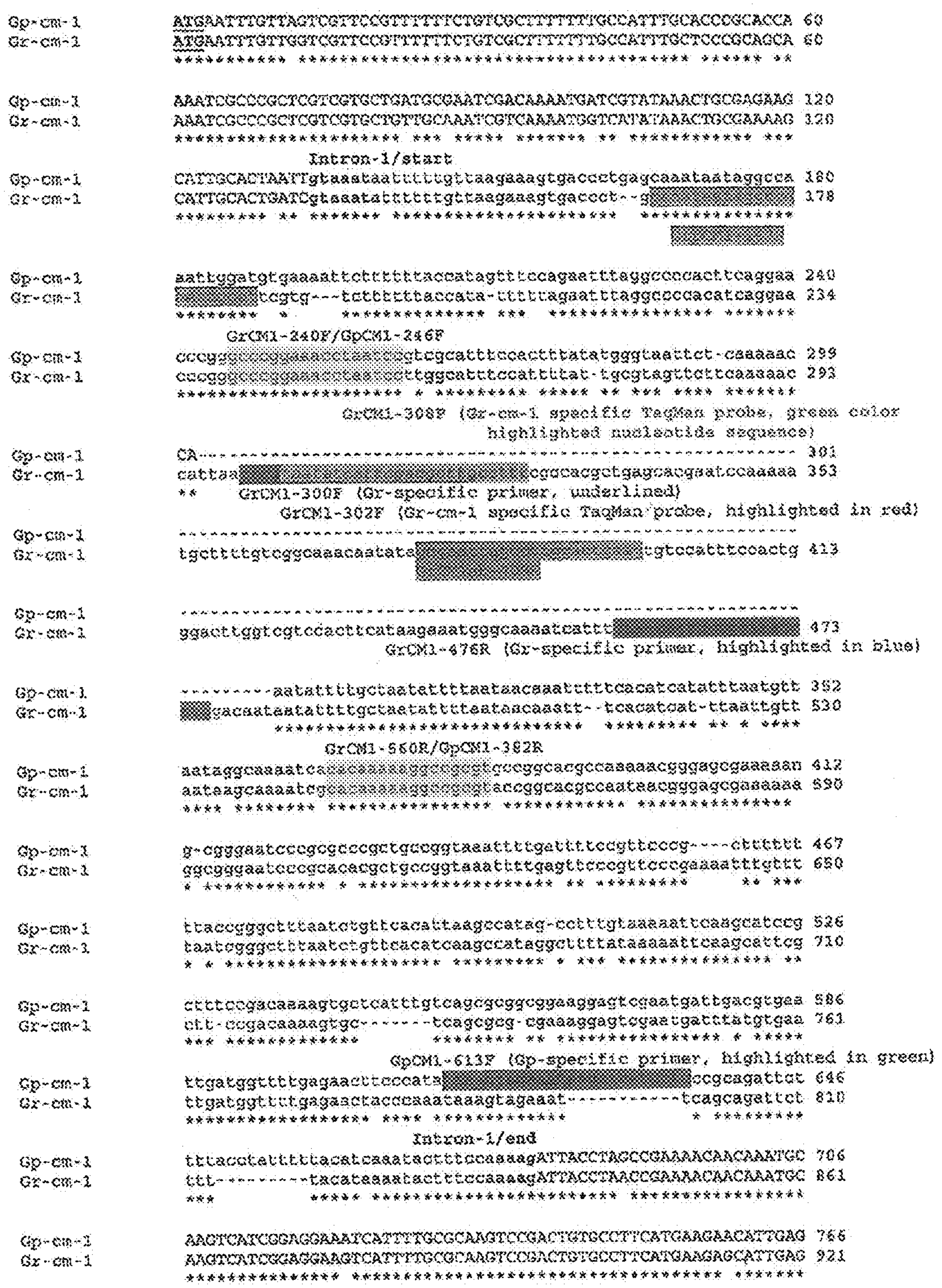
FIG. 1 depicts the genomic DNA sequence alignment between *G. rostochiensis* (Gr-cm-1; SEQ ID NO:1) and *G. pallida* (Gp-cm-1; SEQ ID NO:2) cm genes. Primer and probe locations are indicated in the sequences.

This invention concerns the cloning of the chorismate mutase (cm) gene from *G. rostochiensis*. The cDNA, Gr-cm-1 (SEQ ID NO: 4) and genomic clones, Gr-cm-1A (SEQ ID NO: 1) and Gr-cm-1B (SEQ ID NO: 3) of cm have been isolated. Gr-cm-1 is a parasitism gene that was found to be expressed exclusively within the subventral gland cells of the nematode. Studies from our lab and others concerning the cm gene from other species of the sedentary endoparasitic nematodes have suggested that nematode-secreted chorismate mutase encoded by the cm gene plays critical roles in nematode infection and parasitism of host plants.

We have utilized the cm gene to generate PCR (polymerase chain reaction) primers and probes for specifically identifying *G. rostochiensis*. Polymerase chain reaction (PCR) has been shown to be a highly sensitive and rapid method for detecting and identifying numerous plant pathogens. PCR assays are extremely sensitive and highly specific for the pathogen in question and results can be obtained within a relatively short period of time, usually within a day. The invention provides for PCR primers and probes, methods, and kits useful for detecting *G. rostochiensis*, and further, for differentiating *G. rostochiensis* from other *Globodera* species, particularly from *G. pallida*.

Several primers and primer sets have been identified as effective for amplifying particular *Globodera* species and to differentiate between species, using standard PCR and the TaqMan PCR assay. The nucleotide sequence of the 1973 bp chorismate mutase gene of *G. rostochiensis* was determined. This cm genomic DNA region was targeted to use to discriminate species of Globodera. Among the *G. rostochiensis* isolates or the *G. pallida* isolates, there is a greater than 99% identity within this region as determined by the Bestfit program of the Genetics Computer Group computer package (Version 9.0). When comparing the *G. rostochiensis* with the *G. pallida* isolates, an approximately 13% divergence was observed; this calculation does not include a unique insertion located in the first intron of Gr-cm-1 and another unique insertion located in the third intron of Gp-cm-1. Unique PCR primers were derived from sequences of this cm genomic DNA region for rapid identification of *Globodera* species. These primers should prove useful for direct detection of the *G. rostochiensis* parasite for eradication and quarantine purposes.

A primer can preferably be about sixteen to twenty-four nucleotides long. Primers can hybridize to the DNA strand of a target sequence and are designated sense primers. Primers can hybridize to the DNA strand that is the complement of a target sequence; such primers are designated anti-sense primers. Primers that hybridize to each strand of DNA in the same location or to one another are known as complements of one another. Primers can be designed to hybridize to an mRNA sequence complementary to a target DNA sequence and are useful in reverse transcriptase PCR.

The primers can hybridize to the cm target DNA sequence of *G. rostochiensis*. The target DNA sequence is the cm gene of *G. rostochiensis* of approximately 1.9 kb. The primers can preferably hybridize to the *G. rostochiensis* species of *Globodera* and not to other closely related species. The primers can be used in methods and kits for detecting species of *Globodera* in a biological sample, preferably by detecting amplification products using primers that hybridize to the target sequence. The primers of the invention can be used for evaluating and monitoring the efficacy of any treatments utilized to eliminate the pathogenic *G. rostochiensis*. The primers of the invention can be used to form probes.

In brief, the DNA amplification products can be detected by (a) providing a biological sample comprising extracted DNA; (b) amplifying a target sequence of the DNA to provide DNA amplification products carrying a selected target DNA sequence; and (c) detecting the presence of *G. rostochiensis* and *G. pallida* species by detecting the presence of the DNA amplification products.

The biological sample may be extracted genomic DNA. The biological sample may be a test sample containing extracted DNA. Therefore, currently, extracted DNA is utilized to detect DNA amplification products.

In one method, the enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide or by hybridization to a probe. In an alternative embodiment, at least one probe that hybridizes to the amplified products is labeled with a biotin moiety and/or at least one probe labeled with fluorescently-labeled probe. The hybrids are then bound to a solid support such as a bead, multiwell plate, dipstick or the like that is coated with streptavidin. The presence of bound hybrids can be detected using an antibody to the fluorescent tag conjugated to horseradish peroxidase. The enzymatic activity of horseradish peroxidase can be detected with a colored, luminescent or fluorimetric substrate. Conversion of the substrate to product can be used to detect and/or measure the presence of *G. rostochiensis* PCR products.

An oligonucleotide primer preferably has a gene sequence that hybridizes to a sequence flanking one end of the DNA sequence to be amplified. The DNA sequence to be amplified is located adjacent the attachment of the single primer, or between the attachment of the two primers. In the use of a pair of oligonucleotide primers, each of the primers has a different DNA sequence and hybridizes to sequences that flank either end of the target sequence to be amplified. Design of primers and their characteristics have been described previously. The preferred DNA sequences of the oligonucleotide primers and or complements thereof, or mixtures thereof are shown in Example 3. The primers may also be degenerate primers that hybridize to the target DNA sequence under hybridization conditions for a primer of that size and sequence complementarity.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, colorimetric, fluorometric or luminescent signal, or the like. In addition, the gel may be stained during or after electrophoresis with a visualizing dye such as ethidium bromide or silver stain wherein the resulting bands by be visualized under ultraviolet light.

To conclusively prove the identity of the amplified DNA product, a Southern blot assay should be conducted. The amplified products are separated by electrophoresis on a polyacrylamide or agarose gel, transferred to a membrane such as a nitrocellulose or nylon membrane, reacted with an oligonucleotide probe, and stained as above. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

In addition to developing classical PCR assays, *Globodera* species-specific PCR primers were used with an internal *G. rostochiensis* or *G. pallida* specific 5'-FAM-labeled oligonucleotide probe sequence in a 5'-fluorogenic TaqMan PCR assay. In most 5'-fluorogenic TaqMan PCR assays, the flanking PCR primers are the same, and the internal fluorescent-labeled probe is designed to be characteristic for a specific sequence (Livak et al. 1995. PCR *Meth. Applic.* 4: 357-362). For TaqMan PCR, the DNA sequences of the oligonucleotide primer sets and or complements thereof, or mixtures thereof are shown in Example 3. An internal oligonucleotide, a 23-mer probe, labeled with the chromophore FAM-TAATATCATTCGACGCTTGCCTT-TAMRA (SEQ ID NO: 12) and the primers GrCM1-240F (=GpCM1-246F): GCCCGGAAACCTAATCC (SEQ ID NO: 6) and GrCM1-560R (=GpCM1-382R): ACGCGGCCTTTTTGTG (SEQ ID NO: 7) provide specificity for *G. rostochiensis* isolates. A 26-mer probe, labeled with the chromophore FAM-TGAAGCGCTGTTCTTTCAATAAATTA-TAMRA (SEQ ID NO: 15) and the primers GpCM-1079F (=GrCM-1290F): GACGCTAACAAAGTCATTCAG (SEQ ID NO: 13) and GpCM-1357R (=GrCM-1475R): AAATAATTTTGATAACTGCCGAAA (SEQ ID NO: 14) are used for *G. pallida* isolates. Another set of primers and species-specific TaqMan probes used to differentiate *G. rostochiensis* isolates from *G. pallida* isolates are: the TaqMan probe GrCM1-308P: FAM-CATTCGACGCTTGCCTTTCGC-TAMRA (SEQ ID NO: 16) and the primers GrCM1-167F: CAAATAATAGGCCAA ATTGGAT (SEQ ID NO: 17) and GrCM1ab-408R: CTTCAGTCCAAGGCTAATTCTC (SEQ ID NO: 18) are used to identify *G. rostochiensis* isolates and the TaqMan probe GpCM1-1692P: FAM-TCCCTAACGAACTGAGGCTTACCG-TAMRA (SEQ ID NO: 19) and the primers GpCM1-1551F: TGAAGCTTTCGGCAGTTAT (SEQ ID NO: 20) and GpCM1-1811R: GGTGACCGTCTGCAAGT (SEQ ID NO: 21) are used to identify *G. pallida* isolates.

The TaqMan detection assays offer several advantages over the classical PCR assays developed for *G. rostochiensis* and *G. pallida*. First, the TaqMan assays combine the sensitivity of PCR along with hybridization of the internal oligonucleotide sequence that is present in a *G. rostochiensis* or *G. pallida* DNA sequence. Following PCR, samples do not have to be separated on agarose gels, and the subsequent Southern blots and hybridization steps that are necessary to verify the identity of the PCR products are eliminated. These additional post-PCR confirmation steps can easily add several days for an accurate identification. Using the TaqMan system, the *G. rostochiensis*- or *G. pallida*-specific 5'-fluorogenic assays are completed within 2.5 h. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Time can be a very important factor in quarantine procedures. Another advantage of the TaqMan system is the potential for multiplexing. Since different fluorescent reporter dyes can be used to construct probes, several different pathogen systems could be combined in the same PCR reaction, thereby reducing the labor costs that would be incurred if each of the tests were performed individually. The advantages of rapid, conclusive data together with labor and cost efficiency make the TaqMan detection system utilizing the specific primers of the invention a highly beneficial system for eradication and quarantine protocols.

The present invention may be used to reduce crop destruction by the parasitic cyst nematode *Globodera rostochiensis.*

The nucleic acid molecules, constructs and vectors of the invention and the methods of using them can be utilized to induce resistance to *G. rostochiensis* in important food crops. We have used RNAi-based technology to generate nematode-resistant hairy roots. Such technology can be used to generate nematode-resistant plants as a strategy to provide broad resistance in potato plants against *Globodera pests.*

RNA interference (RNAi) is a process utilizing endogenous cellular pathways whereby a double stranded RNA (dsRNA) specific target gene results in the degradation of the mRNA of interest. In recent years, RNAi has been used to perform gene “knockdown” in a number of species and experimental systems, from the nematode *C. elegans*, to plants, to insect embryos and cells in tissue culture (Fire et al. 1998. *Nature* 391: 806-811; Martinez et al. 2002. *Cell* 110: 563-574; McManus and Sharp. 2002. *Nat. Rev. Genet.* 3: 737-747). RNAi works through an endogenous pathway including the Dicer protein complex that generates about 21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knockdown of mRNA expression is usually sequence specific. The gene silencing effect of RNAi persists for days and, under experimental conditions, can lead to a decline in abundance of the targeted transcript of 90% or more with consequent decline in levels of the corresponding protein.

In accordance with the invention, a parasitic *G. rostochiensis* nematode is contacted with a dsRNA, which specifically inhibits expression of the target gene cm, which is essential for survival, infection and parasitism of host plants. Preferably, the parasitic *G. rostochiensis* nematode comes into contact with the dsRNA after entering a plant, which expresses the dsRNA. In one embodiment, the dsRNA is encoded by a vector, which has been transformed into an ancestor of the infected plant. Preferably, the nucleic acid sequence expressing said dsRNA is under the transcriptional control of a root specific promoter.

Accordingly, the dsRNA of the invention is substantially identical to a portion of the cm target gene of the *G. rostochiensis* genome. Preferably, the dsRNA of the invention comprises (a) a first strand comprising a sequence that is substantially identical to from about 21 to about 702 consecutive nucleotides of the cm target gene and (b) a second strand comprising a sequence substantially complementary to the first strand.

Fragments of dsRNA larger than about 21 nucleotides in length are cleaved intracellularly by nematodes and plants to siRNAs of about 21 nucleotides in length, and these siRNAs are the actual mediators of the RNAi phenomenon. Example 4 demonstrates that siRNAs are generated when a vector containing the *G. rostochiensis* cm target gene is transformed into tomato hairy roots. The cyst count is reduced when *G. rostochiensis* is inoculated onto transgenic tomato hairy roots expressing a dsRNA comprising one strand that is identical to a portion of the *G. rostochiensis* cm target gene, as compared to a *G. rostochiensis*-inoculated transgenic control hairy root line that contains the empty vector and does not contain a dsRNA comprising one strand that is substantially identical to a portion of the *G. rostochiensis* cm target gene. Thus the dsRNA of the present invention may range in length from about 21 nucleotides to about 702 nucleotides.

dsRNA containing a nucleotide sequence identical to a portion of the *G. rostochiensis* cm target gene is preferred for inhibition. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for inhibition. Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. *CABIOS* 4: 11-17), the local homology algorithm of Smith et al. (1981. *Adv. Appl. Math.* 2: 482); the homology alignment algorithm of Needleman and Wunsch (1970. *J. Mol. Biol.* 48: 443-453); the search-for-similarity-method of Pearson and Lipman (1988. *Proc. Natl. Acad. Sci.* 85: 2444-2448; the algorithm of Karlin and Altschul (1990. *Proc. Natl. Acad. Sci. USA* 87: 2264), modified as in Karlin and Altschul (1993. *Proc. Natl. Acad. Sci. USA* 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Greater than 90% sequence identity, or even 100% sequence identity, between the inhibitory RNA and the portion of the cm target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 21, 25, 50, 100, 200, 300, 400, 500, 600, 700, 800, or 974 bases. In a preferred embodiment, the length of the double-stranded nucleotide sequence is from approximately from about 21 to about 974 nucleotides in length.

Preferably, the dsRNA molecule of the present invention comprises one strand comprising a sequence substantially identical to a portion of the cm target gene from *G. rostochiensis.*

The dsRNA of the invention may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Higher doses of double-stranded material may yield more effective inhibition.

In another embodiment, the invention provides an isolated recombinant expression vector comprising a nucleic acid encoding a dsRNA molecule as described above, wherein expression of the vector in a host plant cell results in increased resistance to *G. rostochiensis* as compared to a wild-type variety of the host plant cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host plant cell into which they are introduced. Other vectors are integrated into the genome of a host plant cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., potato virus X, tobacco rattle virus, and Geminivirus), which serve equivalent functions.

The recombinant expression vectors of the invention comprise a nucleic acid of the invention in a form suitable for expression of the nucleic acid in a host plant cell, which means that the recombinant expression vector includes one or more regulatory sequences, selected on the basis of the host plant cells to be used for expression, which is operatively linked to the nucleic acid sequence to be expressed.

In accordance with the invention, the recombinant expression vector comprises a regulatory sequence operatively linked to a nucleotide sequence that is a template for one or both strands of the claimed dsRNA. In one embodiment, the nucleic acid molecule further comprises a promoter flanking either end of the nucleic acid molecule, wherein the promoters drive expression of each individual DNA strand, thereby generating two complementary RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated by 3 to 500 base pairs, and wherein after transcription, the RNA transcript folds on itself to form a hairpin. In accordance with the invention, the spacer region in the hairpin transcript may be any DNA fragment.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and be transiently expressed or transiently active. Whether present in an extra-chromosomal non-replicating vector or a vector that is integrated into a chromosome, the polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals.

In accordance with the present invention, the expression cassette comprises an expression control sequence operatively linked to a nucleotide sequence that is a template for one or both strands of the dsRNA. The dsRNA template comprises (a) a first stand having a sequence substantially identical to from about 21 to about 702 consecutive nucleotides of SEQ ID NO: 4; and (b) a second strand having a sequence substantially complementary to the first strand. In further embodiments, a promoter flanks either end of the template nucleotide sequence, wherein the promoters drive expression of each individual DNA strand, thereby generating two complementary RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by 3 to 500 base pairs, and wherein after transcription, the RNA transcript folds on itself to form a hairpin.

The invention is also embodied in a transgenic plant capable of expressing the dsRNA of the invention and thereby inhibiting the cm target gene in *G. rostochiensis*. Suitable methods for transforming or transfecting host cells including plant cells can be found in Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. Any method may be used to transform the recombinant expression vector into plant cells to yield the transgenic plants of the invention.

In accordance with this embodiment, the transgenic plant of the invention is produced by a method comprising the steps of providing a *G. rostochiensis* cm gene, preparing an expression cassette having a first region that is substantially identical to a portion of the cm gene and a second region which is complementary to the first region, transforming the expression cassette into a plant, and selecting progeny of the transformed plant which express the dsRNA construct of the invention.

Increased resistance to *G. rostochiensis* infection is a general trait wished to be inherited into a wide variety of plants, including but not limited to potato, tomato, and eggplant. In a preferred embodiment, the plant is a potato plant.

Preferably, the dsRNA of the invention is introduced into parasitic *G. rostochiensis* when the nematodes ingest transgenic plants containing expression vectors encoding the dsRNA.

As used herein, the term "amount sufficient to inhibit expression" refers to a concentration or amount of the dsRNA that is sufficient to reduce levels or stability of mRNA or chorismate mutase produced from the cm target gene in a parasitic *G. rostochiensis* nematode. As used herein, "inhibiting expression" refers to the absence or observable decrease in the level of protein and/or mRNA product from the cm target gene. Inhibition of the cm target gene expression may be lethal to the parasitic *G. rostochiensis* nematode, or such inhibition may delay or prevent entry into a particular developmental step (e.g., metamorphosis), if plant disease is associated with a particular stage of the parasitic nematode's life cycle. The consequences of inhibition can be confirmed by examination of the outward properties of the nematode (as presented below in Example 5).

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al., supra. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, here the cm enzyme, operably linked to a promoter and/or other regulatory sequences.

As used herein, the term "express" or "expression" is defined to mean transcription alone. The regulatory elements are operably linked to the coding sequence of the cm gene such that the regulatory element is capable of controlling expression of cm gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence which specifically induces the cm gene expression in roots. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

As used herein, the term "expressed sequence tag" (EST) refers to a short strand of DNA (approximately 200 base pairs long) which is part of a cDNA. ESTs provide an indication of the abundance of the genes that are being expressed in that tissue at that stage of development. Because an EST is usually unique to a particular cDNA, and because cDNAs correspond to a particular gene in the genome, ESTs can be used to help identify unknown genes and to map their position in the genome.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143: 277) and particle-accelerated or "gene gun" transformation technology (Klein et al. 1987. *Nature* (*London*) 327: 70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual; Weissbach and Weissbach.* 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The term "substantially pure" as used herein refers to the chorismate mutase (cm) polypeptide that is substantially free of other proteins, lipids, carbohydrates or other materials with which it is naturally associated. One skilled in the art can purify cm using standard techniques for protein purification. The purity of the cm polypeptide can also be determined by amino-terminal amino acid sequence analysis.

The invention includes functional cm polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of cm polypeptide", refers to all fragments of cm that retain chorismate mutase activity. Functional fragments, for example, can vary in size from a polypeptide fragment as small as an epitope capable of binding an antibody molecule, to a large polypeptide capable of participating in the characteristic induction or programming of phenotypic changes within a cell. Furthermore, the function or activity of cm can be utilized in bioassays to identify functional fragments of the chorismate mutase polypeptide or related polypeptides.

Modifications of the chorismate mutase primary amino acid sequence may result in further mutant or variant proteins having substantially equivalent activity to the chorismate mutase polypeptides described herein. Such modifications may be deliberate, as by site-directed mutagenesis, or may occur by spontaneous changes in amino acid sequences where these changes produce modified polypeptides having substantially equivalent activity to the chorismate mutase polypeptides. Any polypeptides produced by minor modifications of the chorismate mutase primary amino acid sequence are included herein as long as the biological activity of chorismate mutase is present.

A heterologous coding sequence refers to coding sequences which encode peptides or proteins, unrelated to, or, other than, the chorismate mutase polypeptides provided above and which are not intrinsically found in the position provided in the chimeric gene construct.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a chorismate mutase polypeptide and which hybridize under stringent conditions, as described herein, to the cm sequences disclosed herein, or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art, as discussed above.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48: 443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular nematode protein. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the chorismate mutase polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, chorismate mutase activity as described herein. Such variants may result from, for example, genetic polymorphism or from human manipulation. Biologically active variants of a native cm protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired chorismate mutase activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of chorismate mutase protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds, suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful cloning of cm is a major step in identifying and differentiating *Globodera* species and in our understanding of the regulatory mechanisms underlying resistance to the potato cyst nematode in plants. Deciphering the mechanism by which this gene functions to result in Ro2-resistant cultivars will aid in devising new strategies and/or control points for eradicating *G. rostochiensis* in crops.

EXAMPLES

Having now generally described this invention, the same will be better understood by reference to certain specific examples, which are included herein only to further illustrate the invention and are not intended to limit the scope of the invention as defined by the claims.

Example 1

Identification and Isolation of *G. Rostochiensis* Cm Target Gene

Gr-cm-1 is a parasitism gene that was found to be expressed exclusively within the subventral gland cells of the nematode. We isolated both the cDNA (Gr-cm-1, SEQ ID NO: 4, GenBank accession number EF437154; to be released) and genomic clones (Gr-cm-1A, SEQ ID NO: 1, GenBank accession number EF437152; Gr-cm-1B, SEQ ID NO: 3, GenBank accession number EF437153; to be released) of the chorismate mutase (CM) gene from *G. rostochiensis.*

Genomic DNA from *G. rostochiensis* was extracted from infective second-stage juveniles of the nematode. The nematode juveniles were lysed with proteinase K and heat treatment and nematode DNA was extracted using phenol and chloroform and finally recovered with ethanol precipitation.

Example 2

DNA Sequencing and Analysis

Plasmid DNA containing the 1973 bp DNA fragment from *G. rostochiensis* was sequenced. Nucleotide sequences from *G. rostochiensis* and *G. pallida* were compared and aligned in our laboratory using the Bestfit and Pileup programs of the Genetics Computer Group computer package (Version 9.0) (Deverex et al. 1984. Nucleic Acids Res. 12: 387-395).

Comparisons between the sequences of the two *Globodera* species, *G. rostochiensis* and *G. pallida*, revealed 227 nucleotide differences within the approximately 1.9 kb region (this calculation does not include unique insertions in intron 1 of Gr-cm-1 and in intron 3 of Gp-cm-1; FIG. 1). Most of the nucleotide differences between *G. rostochiensis* and *G. pallida* were randomly scattered throughout the approximately 1.9 kb region.

Example 3

Selection of Species-Specific Primers and the Development of Polymerase Chain Reaction Assays Although the overall sequence identity is high between *G. rostochiensis* and *G. pallida* within this approximately 1.9 kb region (84% identity), selective PCR primer sites were chosen to distinguish these two *Globodera* species from each other using PCR (FIG. 1).

To obtain different sizes of PCR products from *G. rostochiensis* and *G. pallida*, common primers were selected from within intron 1 of genomic DNA from *G. rostochiensis* (Gr-cm-1; SEQ ID NO: 1) and *G. pallida* (Gp-cm-1; SEQ ID NO: 2). These PCR primers are specific to both potato cyst nematode species: GrCM1-240F (=GpCM1-246F): GCCCGGAAACCTAATCC (SEQ ID NO: 6) and GrCM1-560R (=GpCM1-382R): ACGCGGCCTTTTTGTG (SEQ ID NO: 7). The PCR products recovered from *G. rostochiensis* and *G. pallida* are 321 bp and 137 bp, respectively. Therefore, if a PCR product of about 300 bp is obtained, then the species is *G. rostochiensis*. A PCR product of about 140 bp indicates that the species is *G. pallida*. The obtained PCR products can be sequenced to verify sequence identity.

Species-specific PCR primers for nematode identification were selected from the genomic DNA from *G. rostochiensis* and *G. pallida*. The *G. rostochiensis*-specific PCR primers: GrCM1-300F: TTCGTAATATCATTCGACGCTT (SEQ ID NO: 8) and GrCM1-476R: CAACGTTTCCAGCAATGTTTG (SEQ ID NO: 9) are expected to result in a PCR product of 177 bp. The *G. pallida*-specific PCR primers: GpCM1-829F: GCCCCAACA GCCAACAA (SEQ ID NO: 10) and GpCM1-925R: GATTATAAATTTCACAAATTGTCG (SEQ ID NO: 11) are expected to result in a PCR product of 97 bp.

The quantitative real-time PCR (qPCR) TaqMan assay is a very reliable and quick assay for identifying and differentiating *G. rostochiensis* from *G. pallida*. Using the genomic DNA from *G. rostochiensis* and *G. pallida* as a template, the primers GrCM1-240F (=GpCM1-246F): GCCCGGAAACCTAATCC (SEQ ID NO: 6) and GrCM1-560R (=GpCM1-382R): ACGCGGCCTTTTTGTG (SEQ ID NO: 7), and the Gr-cm-1-specific TaqMan probe-GrCM1-302F: FAM-TAATATCATTCGACGCTTGCCTT-TAMRA (SEQ ID NO: 12), for *G. rostochiensis* identification are identified. The primers for *G. pallida* identification are GpCM-1079F (=GrCM-1290F): GACGCTAAC AAAGTCATTCAG (SEQ ID NO: 13) and GpCM-1357R (=GrCM-1475R): AAATAATTTT GATAACTGCCGAAA (SEQ ID NO: 14); the Gp-cm-1-specific TaqMan probe is GpCM-1263F: FAM-TGAAGCGCTGTTCTTTCAATAAATTA-TAMRA (SEQ ID NO: 15).

Figure 2:
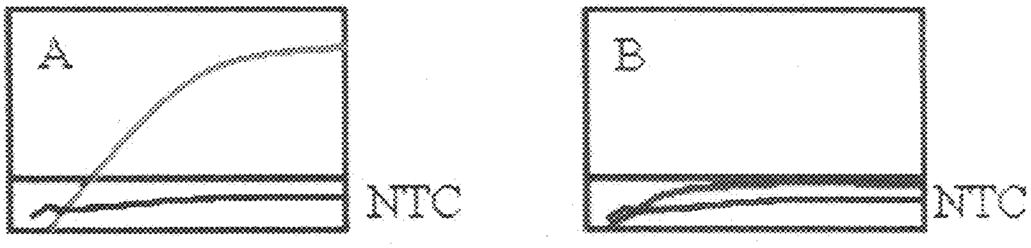
FIGS. 2A and 2B show PCR amplification plots.

When using the primers and probe for *G. rostochiensis* identification, if Graph A (FIG. 2A) is obtained, then the species is *G. rostochiensis*. If Graph B (FIG. 2B) is obtained, then the species is not *G. rostochiensis*. When using the primers and probe for *G. pallida* identification, if Graph A is obtained, then the species is *G. pallida*. If Graph B is obtained, then the species is not *G. pallida*.

In another TaqMan qPCR assay using the genomic DNA from *G. rostochiensis* and *G. pallida* as a template, the primers GrCM1-167F: CAAATAATAGGCCAA ATTGGAT (SEQ ID NO: 17) and GrCM1ab-408R: CTTCAGTCCAAGGCTAATTCTC (SEQ ID NO: 18) and the Gr-cm-1-specific TaqMan probe-GrCM1-308P: FAM-CATTCGACGCTTGCCTTTCGC-TAMRA (SEQ ID NO: 16) are used for *G. rostochiensis* identification. The primers for *G. pallida* identification are GpCM1-1551F: TGAAGCTTTCGGCAGTTAT (SEQ ID NO: 20) and GpCM1-1811R: GGTGACCGTCT GCAAGT (SEQ ID NO: 21); the Gp-cm-1-specific TaqMan probe is GpCM1-1692P: FAM-TCCCTAACGAACTGAGGCTTACCG-TAMRA (SEQ ID NO: 19).

When using the primers and probe for *G. rostochiensis* identification in TaqMan qPCR, if Graph A (FIG. 2A) is obtained, then the species is *G. rostochiensis*. However, if Graph B (FIG. 2B) is obtained, then the species is not *G. rostochiensis*. If Graph A is obtained when the primers and probe for *G. pallida* identification are used, then the species is *G. pallida*. If Graph B is obtained, then the species is not *G. pallida*.

Thus, the TaqMan qPCR approach that we have developed can provide a highly reliable, sensitive, and rapid identification of the two species of the potato cyst nematodes *Globodera rostochiensis* and *G. pallida*.

Example 4

Generation of Transgenic Tomato Hairy-Root

RNA interference (RNAi) is a gene silencing process triggered by double-stranded RNA (dsRNA). Recent work has demonstrated that the expression in a host plant of dsRNA targeting an essential nematode parasitism gene resulted in broad resistance to root knot nematode infection. This plant-delivered RNAi approach represents a viable means of developing broad or increased resistance to cyst nematodes as well.

Figure 3:
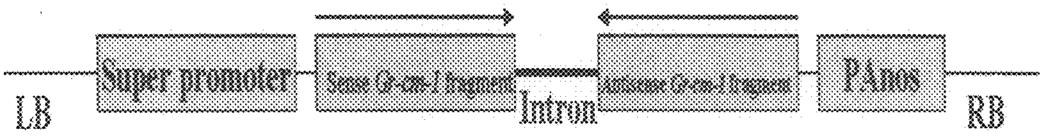
FIG. 3 is an illustration of the T-DNA region of the RNAi vector (pSUPERgus) containing the sense and antisense DNA fragment targeting a 702 bp of the Gr-cm-1 gene (highlighted in yellow in FIG. 4). The T-DNA region is inserted into the plant genome when the plant is transformed with the vector.

Transgenic tomato hairy roots expressing the RNAi construct (FIG. 3) targeting a 702 bp sequence of the Gr-cm-1 gene (FIG. 4) were generated. The cDNA sequence alignment between *G. rostochiensis* (SEQ ID NO: 4) and *G. pallida* (SEQ ID NO: 5) cm genes, the region used for generating dsRNA targeting Gr-cm-1 in transgenic plants, is highlighted in yellow. The 702 bp sense-sequence of the Gr-cm-1 gene was cloned into the XbaI and HindIII sites of the vector and the 702 bp antisense-sequence of the Gr-cm-1 gene was cloned into the Kpnl and Sacl sites of the vector. Generation of transgenic tomato hairy roots was conducted according to the published method (Wang et al. 2007. *Molecular Plant Pathology* 8: 423-436).

A total of 58 transgenic hairy root lines expressing the Gr-cm-1 dsRNA were obtained. A total of 90 transgenic tomato hairy lines expressing only the empty vector were obtained and used as a negative control.

Example 5

Nematode Bioassay

Thirty infective second-stage juveniles of *G. rostochiensis* were inoculated on each transgenic root line grown in the petri-dish and female numbers were counted at 28 days after inoculation of the second-stage juveniles of *G. rostochiensis*. The *G. rostochiensis* juveniles were surface-sterilized and inoculated on transgenic root tips.

Figure 5:
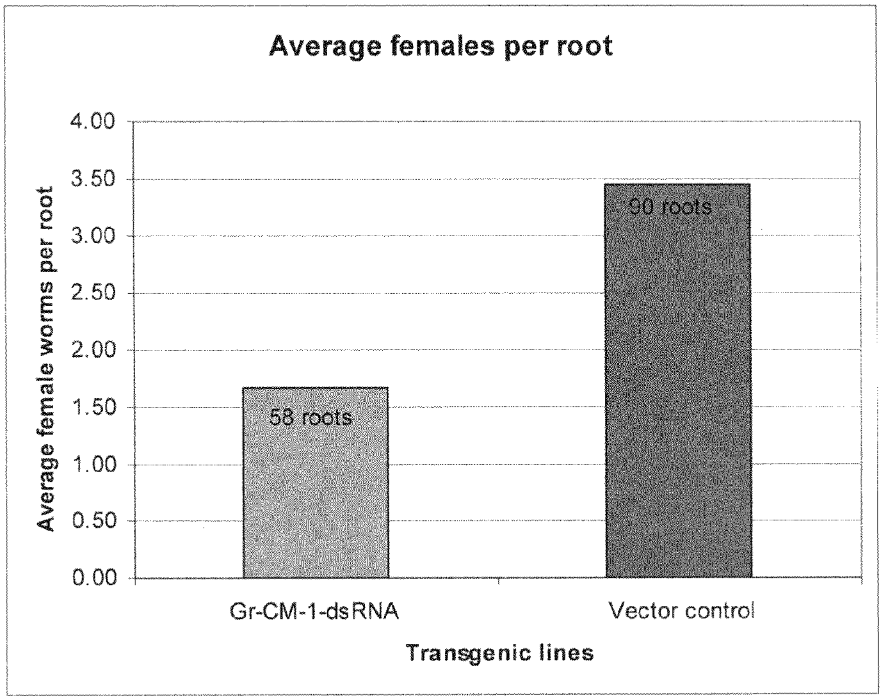
FIG. 5 depicts the average number of females per root developed on transgenic tomato hairy root lines expressing Gr-cm-1 dsRNA or the empty RNAi vector at 28 days after inoculation of the second-stage juveniles of *G. rostochiensis*.

The average number of females developed on transgenic root lines expressing Gr-cm-1 dsRNA was 1.67 per root (FIG. 5), whereas the average number of females developed on transgenic root lines expressing only the empty vector was 3.46 per root (FIG. 5). These results revealed a 52% reduction in the average number of females per root in the Gr-cm-1 dsRNA transgenic lines when compared with the infected control lines.

Our preliminary results suggest that expressing of Gr-cm-1 dsRNA in Ro1 resistant potato cultivars may generate resistance to Ro2 as CM genes from Ro1 and Ro2 are identical. In addition, since CM genes from *G. rostochiensis* and *G. pallida* share a 91.6% nucleotide identity in their open reading frames (FIG. 4), transgenic potatoes expressing Gr-cm-1 dsRNA might have resistance to *G. pallida* as well. Potato plants/cultivars with broad resistance to potato cyst nematode pests are much needed in potato cyst nematode eradication and management strategies.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated polynucleotide consisting of at least 50 contiguous nucleotides of a portion of SEQ ID NO: 4, said portion starting at nucleotide position 58 and ending at nucleotide position 757, wherein uptake by a *G. rostochiensis* nematode of a dsRNA sequence comprising at least one strand that is complementary to said isolated polynucleotide inhibits the growth of said nematode.

2. The isolated polynucleotide of claim 1 operably linked to a heterologous promoter.

3. A plant transformation vector comprising the isolated polynucleotide of claim 1.

4. The plant transformation vector of claim 3 further comprising a reverse fully complementary sequence of said isolated polynucleotide.

5. The plant transformation vector of claim 4, wherein the RNA transcribed from both said isolated polynucleotide and said fully complementary sequence hybridize to form a doubled stranded RNA molecule.

6. The plant transformation vector of claim 3, wherein said polynucleotide sequence is operably linked to a heterologous promoter functional in a plant cell.

7. A cell transformed with the polynucleotide of claim 1.

8. A method for controlling a *G. rostochiensis* parasitic nematode population comprising providing an agent comprising a double stranded ribonucleotide sequence that functions upon being taken up by the nematode to inhibit a biological function within said nematode, wherein the double stranded RNA comprises the isolated polynucleotide of claim 1 and the full complement thereof.

9. A method for controlling a *G. rostochiensis* parasitic nematode population comprising providing an agent comprising a double stranded ribonucleotide sequence that functions upon being taken up by the nematode to inhibit a biological function within said nematode, wherein said double stranded RNA comprises at least 95% nucleotide sequence identity to said isolated polynucleotide of claim 1 and full complement thereof.

* * * * *

SEQUENCE LISTING

```
<160> NUMBER OF SEQ ID NOS: 21

<210> SEQ ID NO 1
<211> LENGTH: 1973
<212> TYPE: DNA
<213> ORGANISM: Globodera rostochiensis

<400> SEQUENCE: 1

atgaatttgt tggtcgttcc gttttttctg tcgctttttt tgccatttgc tcccgcagca      60

aaatcgcccg ctcgtcgtgc tgttgcaaat cgtcaaaatg gtcatataaa ctgcgaaaag     120

cattgcactg atcgtaaata ttttttgtta agaaagtgac cctgcaaata ataggccaaa     180

ttggattcgt gtctttttta ccatattttt agaatttagg ccccacatca ggaacccggg     240

cccggaaacc taatccttgg catttccatt ttattgcgta gttcttcaaa aaccattaat     300

tcgtaatatc attcgacgct tgcctttcgc cacgctgagc acgaatccaa aaatgctttt     360

gtcggcaaac aatatagaga attagccttg gactgaagtg tccatttcca ctgggacttg     420

gtcgtccact tcataagaaa tgggcaaaat catttcaaac attgctggaa acgttggaca     480

ataatatttt gctaatattt taataacaaa tttcacatca tttaattgtt aataagcaaa     540

atcgcacaaa aaggccgcgt accggcacgc caataacggg agcgaaaaaa ggcgggaatc     600

ccgcacacgc tgccggtaaa ttttgagttc ccgttcccga aaatttgttt taatcgggct     660

ttaatctgtt cacatcaagc cataggcttt tataaaaatt caagcattcg cttccgacaa     720

aagtgctcag cgcgcgaaag gagtcgaatg atttatgtga attgatggtt ttgagaacta     780

cccaaataaa gtagaaattc agcagattct ttttacataa aatactttcc aaaagattac     840

ctaaccgaaa acaacaaatg caagtcatcg gaggaagtca ttttgcgcaa gtccgactgt     900

gccttcatga agagcattga ggatggattc aaatttgttg ttgggatgga aggccaaacg     960

gaaacggaat cgacaacggg aaataatatt tttatgtgtt gtaagccgaa tcaaggtacg    1020

gtcactaaat ggaaagaaaa atcttttcga tttgaccatt ttttgcccgt ctgtaaccat    1080

tttgaccaga gacggccact ctcttcattg tcggcatggc caacaaacgg ctgatgttgg    1140

ccaaagatgt ggttctctac aagtacatca acaacaatag cattgacgat ttcgagcggg    1200
```

-continued aaaaggttgt gctgcaaaat gttttggctc aggcgaagag tgccgggata agcgacaact 1260
acggggagcc gtttttccaa gaccaaatgg acgctaacaa agtcattcag gtaaaaaagg 1320
tttaggttta attaacatat ttaaaaattg tggagaagat ctgtttagtg ccaacgacat 1380
ttgaagcgca attaaatcac aatttattgc ccagcgctta ataatctcta attgcttctt 1440
cccatttgaa gttttcggca gttatcaaaa ttatttgttt gggtggttga caaaaagcta 1500
aagcgcttca aattcctatc gaattgaata gtgaggcgta ccgtgaaacc ttttgtagaa 1560
gggctacgtg aagatgtgga acatcggagg gccgtcgccg tctcagacgg tgcccgacct 1620
gcagacgatc acccgtccca aggtgacgga ggcaactgcc gacatggtat tggcactgaa 1680
aaccttccaa acgtttcgca acaaatcgaa ttgttggcgt ttgctggaac ataaacagac 1740
aatgaccggc aatttctga gtttgaacga gccgaacggt gtggacgcct tccgaaaagc 1800
ggtggtccga ctgtgcggcc aggagccgaa acaaaacaca gtgcacgaca ttgacgagca 1860
ggccaagaaa ctgctgaatg aatgacccga cggaatatgt gtcaaccaat ttagtgtgat 1920
ttatttagat cctacgccct atgtgtggag attagatgaa gtaaaaacct gac 1973

<210> SEQ ID NO 2
<211> LENGTH: 1854
<212> TYPE: DNA
<213> ORGANISM: Globodera pallida

<400> SEQUENCE: 2
atgaatttgt tagtcgttcc gtttttctg tcgcttttt tgccatttgc acccgcacca 60
aaatcgcccg ctcgtcgtgc tgatgcgaat cgacaaaatg atcgtataaa ctgcgagaag 120
cattgcacta attgtaaata atttttgtta agaaagtgac cctgagcaaa taataggcca 180
aattggatgt gaaaattctt ttttaccata gtttccagaa tttaggcccc acttcaggaa 240
cccgggcccg gaaacctaat ccgtcgcatt tccactttat atgggtaatt ctcaaaaacc 300
aaatattttg ctaatatttt aataacaaat ttttcacatc atatttaatg ttaataggca 360
aaatcacaca aaaaggccgc gtgccggcac gccaaaaacg ggagcgaaaa aagcgggaat 420
cccgcgcccg ctgccggtaa attttgattt tccgttcccg ctttttttta ccgggcttta 480
atctgttcac attaagccat agcctttgta aaaattcaag catccgcttt ccgacaaaag 540
tgctcatttg tcagcgcggc ggaaggagtc gaatgattga cgtgaattga tggttttgag 600
aacttcccat ataaagtaga aataagctaa tcctcccgca gattctttta cctattttta 660
catcaaatac tttccaaaag attacctagc cgaaaacaac aaatgcaagt catcggagga 720
aatcattttg cgcaagtccg actgtgcctt catgaagaac attgagaatg gactcaaatt 780
tgttgttggg atggaaggcc aaacggaaac ggaatcccca acggaaaacg ccccaacagc 840
caacaataat aattttatgt gttgtaagcc aaatcaaggt acggtcacta aacggaaaga 900
cgacaatttg tgaaatttat aatcttttcg atatggtcat tttttgggcc gtctgtaacc 960
attttcacca gagacggcca cactcttcat tgtcggcgtg gccagcaaac ggctgatgtt 1020
ggccaaagac gtggctctct acaagtacat caacaacaat agcattgacg attttgagcg 1080
tgaaaaggtt gtgttgcaaa atgttttggc tcaagcgaaa agtgccggca taagcgacaa 1140
ctacggggag ccgttcttcc aagaccaaat ggacgctaac aaagtcattc aggtaaaaaa 1200
ggtttaggct taattaacat atttaaaatt gtggaccaga tctgttcggt accagcgaca 1260
tttgaagcgc tgttctttca ataaattaaa tgacaattta ttgcccaggg gcttaatatt 1320
ctcaaattgc ttcttctcat ttgaagcgct gttctttcaa taaattaaat aacaatttat 1380

-continued

```
tgcccagggg cttaatattc tcaaattgct tcttctcatt tgaagctttc ggcagttatc   1440

aaaattattt gtttgattgg ttgagaaaaa gctacagcgc ttcaaatttc cctaacgaac   1500

tgaggcttac cgggaaactt tttgtagaag ggctacgtga agacgtggaa catcaaaggg   1560

tcgtcgccgt ctcagacagt gcccgacttg cagacggtca cccgtcccaa agtgacggag   1620

gcaacagccg acatggtgtt ggcactgaaa acgttccaat tgtttcgtaa caaatcgaat   1680

tgttggagtt tgctggaaca taaacagaca atgaccggca attttctgag tttgaacgag   1740

ccgaacggtg tggaagcctt ccgaaaagcg gtggtccgac tgtgtggcca ggaaccggaa   1800

caaaacacag tgcacgccat tgacgaaaag gccaagaaac tgctgaatga atga         1854
```

```
<210> SEQ ID NO 3
<211> LENGTH: 1913
<212> TYPE: DNA
<213> ORGANISM: Globodera rostochiensis

<400> SEQUENCE: 3

atgaatttgt tggtcgttcc gttttttctg tcgctttttt tgccatttgc tcccgcagca     60

aaatcgcccg ctcgtcgtgc tgttgcaaat cgtcaaaatg gtcatataaa ctgcgaaaag    120

cattgcactg atcgtaaata ttttttgtta agaaagtgac cctgcaaata ataggccaaa    180

ttggattcgt gtctttttta ccatattttt agaatttagg ccccacatca ggaacccggg    240

cgcggaaacc taatccttgg catttccatt ttattgcgta gttcttcaaa aaccattaat    300

tcgtaatatc attcgacgcc ttgcctttcg ccacgctgag cacgaatcca aaaatgcttt    360

tgtcggcaaa caatatagag aattagcctt ggactgaagt gtccatttcc actgggactt    420

ggtcgtccac ttcataagaa atcggcaaaa tcatttcaaa cattgctgga aagagagaag    480

cgaaaagaga agaaagaaga agctggcact ggaagtgatc gaatcggcaa tctcggcgac    540

gcagctgttc aagagaagaa gcgaacgagg gcgttcgcac agtgagggcc ggacactggt    600

ccggtcaacc agagacgccg gttcaattcc ggcccgcccc caagtttttc cctcaaaagc    660

tcccagcact cgttactttc aagtcgaatg atttatgtga attgatggtt ttgagaacta    720

cccaaataaa gtagaaattc agcagattct ttttacataa aatacttacc aaaagattac    780

ctaaccgaaa acaacaaatg caagtcatcg gaggaagtca ttttgcgcaa gtccgactgt    840

gccttcatga agagcattga ggatggattc aaatttgttg ttgggatgga aggccaaacg    900

gaaacggaat cgacaacggg aaataatatt tttatgtgtt gtaagccgaa tcaaggtacg    960

gtcactaaat ggaaagaaaa atcttttcga tttgaccatt ttttgcccgt ctgtaaccat   1020

tttgaccaga gacggccact ctcttcattg tcggcatggc caacaaacgg ctgatgttgg   1080

ccaaagacgt ggttctctac aagtacatca acaacaatag cattgacgat ttcgagcggg   1140

aaaaggttgt gctgcaaaat gttttggctc aggcgaagag tgccgggata agcgacaact   1200

acggggagcc gtttttccaa gaccaaatgg acgctaacaa agtcattcag gtaaaaaagg   1260

tttaggttta attaacatat ttaaaaattg tggagaagat ctgttcggtg ccaacgacat   1320

ttgaagcgca attaaatcac aatttattgc ccagcgctta ataatctcta attgcttctt   1380

cccatttgaa gttttcggca gttatcaaaa ttatttgttt gggtggttga caaaaagcta   1440

aagcgcttca aattcctatc gaattgaata gtgaggcgta ccgtgaaacc ttttgtagaa   1500

gggctacgtg aagatgtgga acatcggagg gccgtcgccg tctcagacgg tgcccgacct   1560

gcagacgatc acccgtccca aggtgacgga ggcaactgcc gacatggtat tggcactgaa   1620

aaccttccaa acgtttcgca acaaatcgaa ttgttggcgt ttgctggaac ataaacagac   1680
```

-continued

```
aatgaccggc aattttctga gtttgaacga gccgaacggt gtggacgcct tccgaaaagc   1740

ggtggtccga ctgtgcggcc aggagccgaa acaaaacaca gtgcacgaca ttgacgagca   1800

ggccaagaaa ctgctgaatg aatgacccga cggaatatgt gtcaaccaat ttagtgtgat   1860

ttatttagat cctacgccct atgtgtggag attagatgaa gtaaaaacct gac          1913
```

<210> SEQ ID NO 4
<211> LENGTH: 992
<212> TYPE: DNA
<213> ORGANISM: Globodera rostochiensis

<400> SEQUENCE: 4

```
ggtttaatta cccaagtttg agaacaatga atttgttggt cgttccgttt tttctgtcgc     60

tttttttgcc atttgctccc gcagcaaaat cgcccgctcg tcgtgctgtt gcaaatcgtc    120

aaaatggtca tataaactgc gaaaagcatt gcactgatca ttacctaacc gaaaacaaca    180

aatgcaagtc atcggaggaa gtcattttgc gcaagtccga ctgtgccttc atgaagagca    240

ttgaggatgg attcaaattt gttgttggga tggaaggcca aacggaaacg gaatcgacaa    300

cgggaaataa tatttttatg tgttgtaagc cgaatcaaga gacggccact ctcttcattg    360

tcggcatggc caacaaacgg ctgatgttgg ccaaagatgt ggttctctac aagtacatca    420

acaacaatag cattgacgat ttcgagcggg aaaaggttgt gctgcaaaat gttttggctc    480

aggcgaagag tgccgggata agcgacaact acggggagcc gtttttccaa gaccaaatgg    540

acgctaacaa agtcattcag aagggctacg tgaagatgtg gaacatcgga gggccgtcgc    600

cgtctcagac ggtgcccgac ctgcagacga tcacccgtcc caaggtgacg gaggcaactg    660

ccgacatggt attggcactg aaaaccttcc aaacgtttcg caacaaatcg aattgttggc    720

gtttgctgga acataaacag acaatgaccg gcaattttct gagtttgaac gagccgaacg    780

gtgtggacgc cttccgaaaa gcggtggtcc gactgtgcgg ccaggagccg aaacaaaaca    840

cagtgcacga cattgacgag caggccaaga aactgctgaa tgaatgaccg acggaatatg    900

tgtcaaccaa tttagtgtga tttatttaga tcctacgccc tatgtgtgga gattagatga    960

agtaaaaacc tgacaaaaaa aaaaaaaaaa aa                                  992
```

<210> SEQ ID NO 5
<211> LENGTH: 1011
<212> TYPE: DNA
<213> ORGANISM: Globodera pallida

<400> SEQUENCE: 5

```
ggtttaatta cccaagtttg agaaaaatga atttgttagt cgttccgttt tttctgtcgc     60

tttttttgcc atttgcaccc gcaccaaaat cgcccgctcg tcgtgctgat gcgaatcgac    120

aaaatgatcg tataaactgc gagaagcatt gcactaatta ttacctagcc gaaaacaaca    180

aatgcaagtc atcggaggaa atcattttgc gcaagtccga ctgtgccttc atgaagaaca    240

ttgagaatgg actcaaattt gttgttggga tggaaggcca aacggaaacg gaatccccaa    300

cggaaaacgc cccaacagcc aacaataata attttatgtg ttgtaagcca aatcaagaga    360

cggccacact cttcattgtc ggcgtggcca gcaaacggct gatgttggcc aaagacgtgg    420

ctctctacaa gtacatcaac aacaatagca ttgacgattt tgagcgtgaa aaggttgtgt    480

tgcaaaatgt tttggctcaa gcgaaaagtg ccggcataag cgacaactac ggggagccgt    540

tcttccaaga ccaaatggac gctaacaaag tcattcagaa gggctacgtg aagacgtgga    600

acatcaaagg gtcgtcgccg tctcagacag tgcccgactt gcagacggtc acccgtccca    660
```

-continued

```
aagtgacgga ggcaacagcc gacatggtgt tggcactgaa aacgttccaa ttgtttcgta    720

acaaatcgaa ttgttggagt ttgctggaac ataaacagac aatgaccggc aattttctga    780

gtttgaacga gccgaacggt gtggaagcct tccgaaaagc ggtggtccga ctgtgtggcc    840

aggaaccgga acaaaacaca gtgcacgcca ttgacgaaaa ggccaagaaa ctgctgaatg    900

aatgacccga cggaattgtg ccaaccaatt tggtgtgatt tatttggatc ctaaacccct    960

atgtttggag attagctgtt agtaaaaact taccattcga caaaaaaaaa a           1011


<210> SEQ ID NO 6
<211> LENGTH: 17
<212> TYPE: DNA
<213> ORGANISM: Artificial Sequence
<220> FEATURE:
<223> OTHER INFORMATION: Globodera rostochiensis and Globodera pallida

<400> SEQUENCE: 6

gcccggaaac ctaatcc                                                    17


<210> SEQ ID NO 7
<211> LENGTH: 16
<212> TYPE: DNA
<213> ORGANISM: Artificial Sequence
<220> FEATURE:
<223> OTHER INFORMATION: Globodera rostochiensis and Globodera pallida

<400> SEQUENCE: 7

acgcggcctt tttgtg                                                     16


<210> SEQ ID NO 8
<211> LENGTH: 22
<212> TYPE: DNA
<213> ORGANISM: Globodera rostochiensis

<400> SEQUENCE: 8

ttcgtaatat cattcgacgc tt                                              22


<210> SEQ ID NO 9
<211> LENGTH: 21
<212> TYPE: DNA
<213> ORGANISM: Globodera rostochiensis

<400> SEQUENCE: 9

caacgtttcc agcaatgttt g                                               21


<210> SEQ ID NO 10
<211> LENGTH: 17
<212> TYPE: DNA
<213> ORGANISM: Globodera pallida

<400> SEQUENCE: 10

gccccaacag ccaacaa                                                    17


<210> SEQ ID NO 11
<211> LENGTH: 24
<212> TYPE: DNA
<213> ORGANISM: Globodera pallida

<400> SEQUENCE: 11

gattataaat ttcacaaatt gtcg                                            24


<210> SEQ ID NO 12
<211> LENGTH: 23
<212> TYPE: DNA
```

-continued

<213> ORGANISM: Globodera rostochiensis

<400> SEQUENCE: 12
taatatcatt cgacgcttgc ctt 23

<210> SEQ ID NO 13
<211> LENGTH: 21
<212> TYPE: DNA
<213> ORGANISM: Artificial Sequence
<220> FEATURE:
<223> OTHER INFORMATION: Globodera rostochiensis and Globodera pallida

<400> SEQUENCE: 13
gacgctaaca aagtcattca g 21

<210> SEQ ID NO 14
<211> LENGTH: 24
<212> TYPE: DNA
<213> ORGANISM: Artificial Sequence
<220> FEATURE:
<223> OTHER INFORMATION: Globodera rostochiensis and Globodera pallida

<400> SEQUENCE: 14
aaataatttt gataactgcc gaaa 24

<210> SEQ ID NO 15
<211> LENGTH: 26
<212> TYPE: DNA
<213> ORGANISM: Globodera pallida

<400> SEQUENCE: 15
tgaagcgctg ttctttcaat aaatta 26

<210> SEQ ID NO 16
<211> LENGTH: 21
<212> TYPE: DNA
<213> ORGANISM: Globodera rostochiensis

<400> SEQUENCE: 16
cattcgacgc ttgcctttcg c 21

<210> SEQ ID NO 17
<211> LENGTH: 22
<212> TYPE: DNA
<213> ORGANISM: Globodera rostochiensis

<400> SEQUENCE: 17
caaataatag gccaaattgg at 22

<210> SEQ ID NO 18
<211> LENGTH: 22
<212> TYPE: DNA
<213> ORGANISM: Globodera rostochiensis

<400> SEQUENCE: 18
cttcagtcca aggctaattc tc 22

<210> SEQ ID NO 19
<211> LENGTH: 24
<212> TYPE: DNA
<213> ORGANISM: Globodera pallida

<400> SEQUENCE: 19
tccctaacga actgaggctt accg 24

-continued

```
<210> SEQ ID NO 20
<211> LENGTH: 19
<212> TYPE: DNA
<213> ORGANISM: Globodera pallida

<400> SEQUENCE: 20

tgaagctttc ggcagttat                                         19


<210> SEQ ID NO 21
<211> LENGTH: 17
<212> TYPE: DNA
<213> ORGANISM: Globodera pallida

<400> SEQUENCE: 21

ggtgaccgtc tgcaagt                                           17
```